United States Patent [19]

Korpman

[11] 4,166,464
[45] Sep. 4, 1979

[54] ABSORBENT DRESSING

[75] Inventor: Ralf Korpman, Bridgewater, N.J.

[73] Assignee: Johnson & Johnson, New Brunswick, N.J.

[21] Appl. No.: 796,794

[22] Filed: May 13, 1977

Related U.S. Application Data

[63] Continuation-in-part of Ser. No. 699,104, Jun. 23, 1976, abandoned.

[51] Int. Cl.² ............................................. A61F 17/18
[52] U.S. Cl. .................................... 128/287; 128/156
[58] Field of Search ............................... 128/287, 156

[56] References Cited

U.S. PATENT DOCUMENTS

| | | | |
|---|---|---|---|
| 3,610,244 | 10/1971 | Jones, Sr. ............................ | 128/287 |
| 3,886,941 | 6/1975 | Duane et al. ........................ | 128/287 |
| 3,967,623 | 7/1976 | Butterworth et al. ............... | 128/287 |
| 3,981,306 | 9/1976 | Krusko .............................. | 128/290 P |

Primary Examiner—Robert W. Michell
Assistant Examiner—Milford Juten

[57] ABSTRACT

A highly conformable laminated absorbent dressing which comprises an absorbent pad or layer and an elastic backing film which is both elastic and easily deformable and which preferably is highly thermoplastic and easily heat-sealable. The backing film possesses an elastic recovery from 50 percent stretch of at least about 75 percent, preferably at least about 90 percent; a rubber modulus of not above about 2,000, preferably not above about 1,000, pounds per square inch at 50 percent elongation; a Gurley stiffness of not above about one at a thickness of one mil; and preferably is adapted to form permanent heat seals to paper or boxboard at peak temperatures not above about 350° F. in no more than 4 seconds of clamping time. Various other relationships between the backing film of this invention, the absorbent pad and various types of facing layers are described and claimed.

23 Claims, 18 Drawing Figures

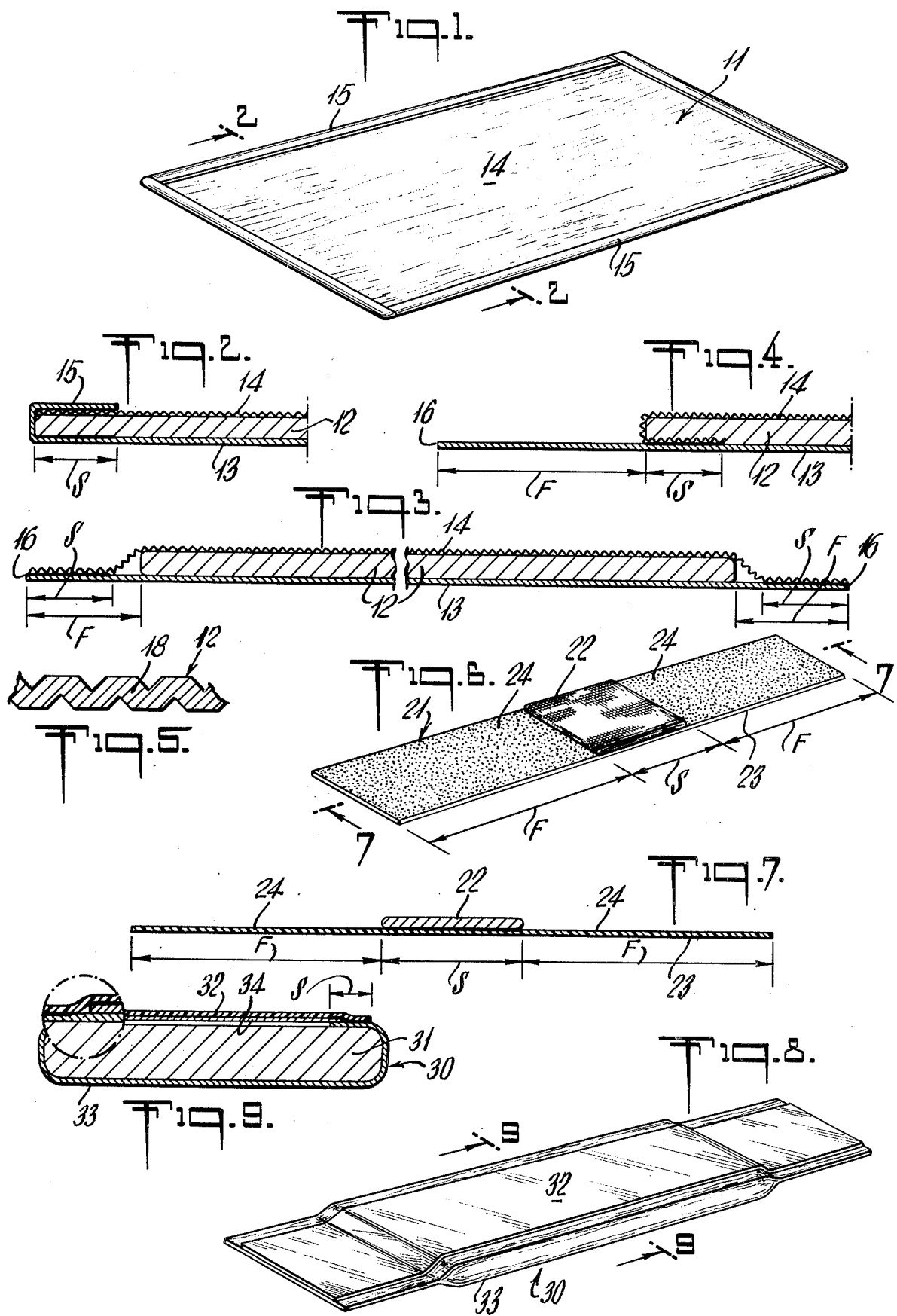

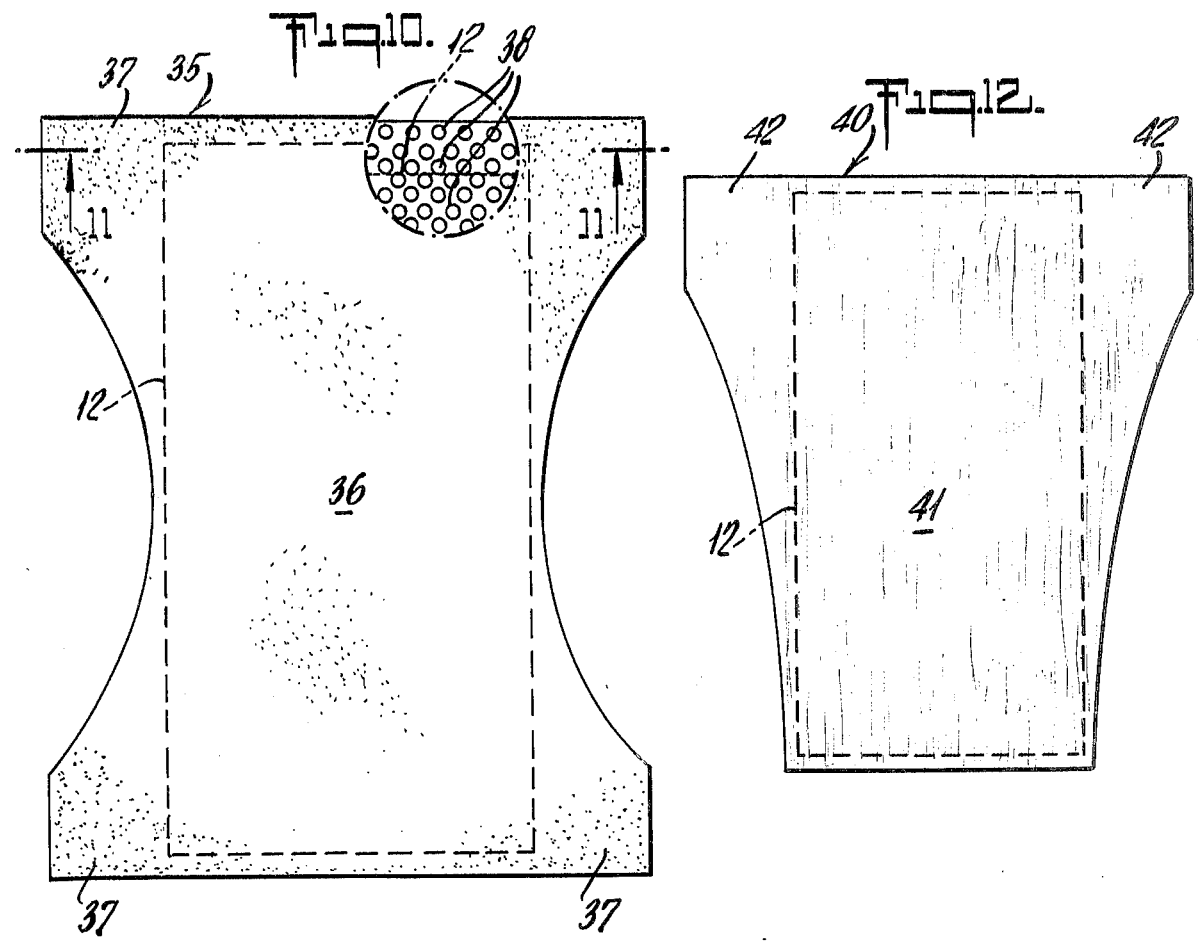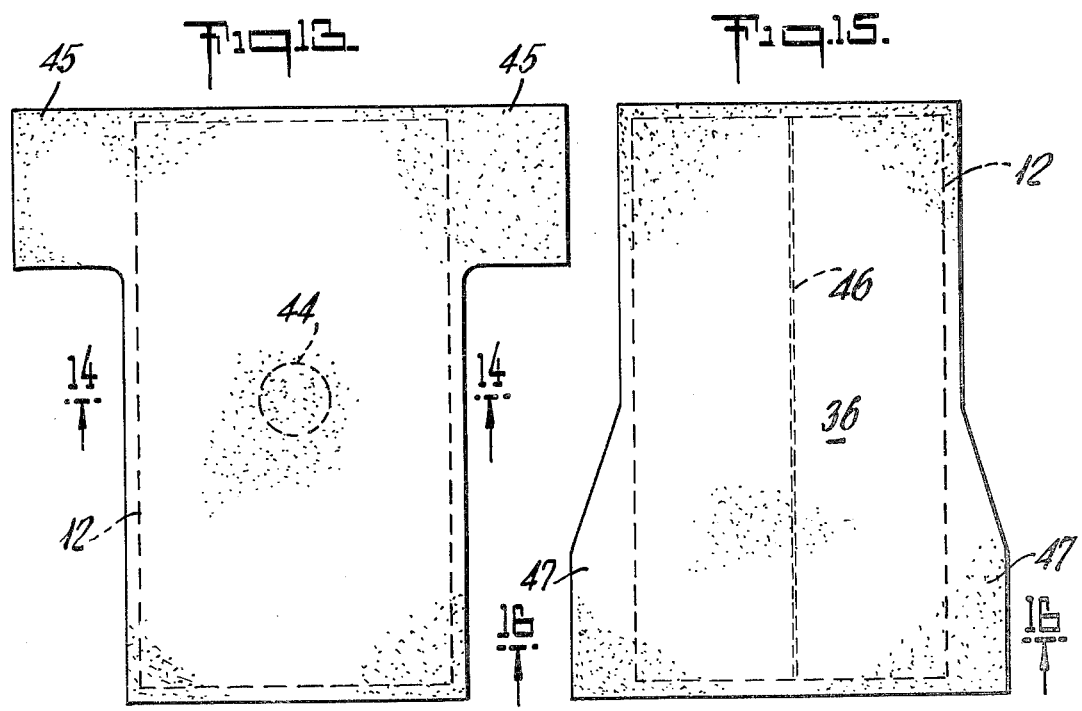

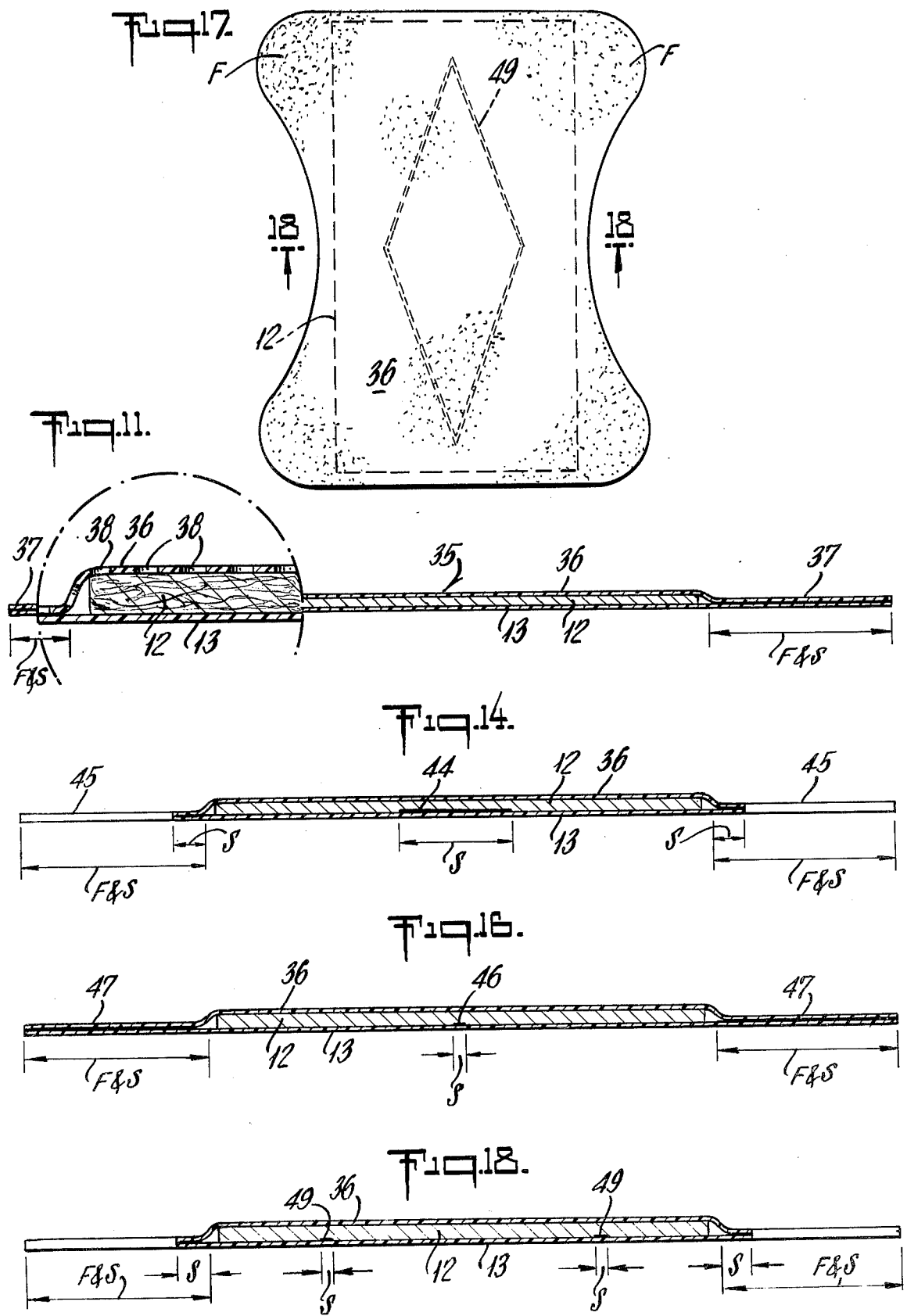

ABSORBENT DRESSING

This application is a continuation-in-part of my copending application Ser. No. 699,104, filed June 23, 1976, now abandoned.

The present invention relates to absorbent dressings including diapers, surgical and first aid dressings, catamenial dressings, and the like; more particularly to such dressings which comprise an absorbent layer laminated to a "plastic" film.

Diapers, hospital pads, sanitary napkins, adhesive bandages, and other dressings for surgical and other uses have been produced by lamination in this way and sold in great quantities principally as disposable products which are used once and then disposed of. In general these products have been somewhat stiff and paper-like and incapable of stretching to any extent, i.e., they have lacked elasticity and conformability to the body members to which they are applied. To a large extent the properties of the dressing have been limited by the properties of its "plastic" backing film. The effect of the backing film of course, is in part a function of the laminated structure of the particular dressing. For instance, the backing film of an adhesive bandage or a disposable diaper normally plays a more dominant role in determining the conformability of the product than that of a sanitary napkin.

I have determined that a superior conformable laminated absorbent dressing can be produced if the backing is elastic and easily stretchable, as well as highly flexible. It also is highly advantageous for many purposes if the backing film is highly thermoplastic and easily heat-sealable.

I have invented a highly conformable absorbent dressing wherein the backing film possesses an elastic recovery from 50 percent stretch of at least about 75 percent, preferably at least about 90 percent; a 50 percent rubber modulus of not above about 2,000, preferably not above about 1,000, pounds per square inch at 50 percent elongation; and a Gurley stiffness of not above about one at a thickness of one mil. This is a highly flexible, easily stretchable film which is elastic and tends to return to its original configuration when in a diaper and stretched around a baby for example. However, since the film has a low modulus it stretches easily and will not grip the baby too tightly either during stretching or after it is secured in position.

Preferably the backing film of the dressing of my invention is highly thermoplastic and easily heat-sealable, i.e., it is adapted to form permanent heat seals to substrates such as paper and boxboard at relatively low heat sealing peak temperatures, generally not above about 350° F., in less than 4 seconds of clamping time, as described more fully hereinafter. It also preferably is capable of high elongation before breaking, i.e., it possesses an elongation to break of at least about 300 percent, preferably at least about 400 percent.

The preferred film of my invention is formed from an elastomeric and thermoplastic film forming composition which comprises an elastomeric component and 0-200 parts, preferably 85-200 parts of a resin component per one hundred parts by weight of the elastomeric component. The elastomeric component consists essentially of linear or radial A-B-A block copolymers or mixtures of these linear or radial A-B-A block copolymers with simple A-B block copolymers. In these block copolymers the A-blocks are derived from styrene or styrene homologues and the B-blocks are derived from conjugated dienes or lower alkenes. The resin component consists essentially of low molecular weight resins, preferably having a number average molecular weight not above about 3,000, and which are adapted to associate principally with the thermoplastic A-blocks of the said block copolymers.

The above film may be extruded hot from particulate, solid or liquid film forming components, cast from a hot melt, formed by coating from solution, or the like. It preferably is extruded from dry particles. The film then is laminated with a layer of absorbent material which may comprise paper, wood pulp or other absorbent material and preferably is configured so as to be extensible, such as by creping. In one preferred form of the invention, the backing film is heat sealed to the absorbent layer by using the high sealing properties of the backing film, itself. The heat seals may be formed only at the corners of the dressing or otherwise spaced from one another for increased flexibility. In dressings, such as disposable diapers, the side of the absorbent layer opposite to the backing normally is covered with a highly porous facing sheet of paper or nonwoven fabric. The corners of such a diaper may be heat sealed together by using the backing of this invention as the heat sealing medium.

In another preferred form of the dressing of this invention, the backing film and the absorbent layer or pad are assembled in such a way that portions of the backing film are extensible independently of the absorbent layer in the direction of their interface. Thus, these portions can be stretched without stretching the absorbent pad so that the pad need not be extensible. For instance, the backing film may extend beyond the edges of the absorbent pad to form flaps on either side of the dressing which are extensible independently of the absorbent pad or that portion of the backing which is directly attached to the pad, or the absorbent pad may be attached to the backing over only a limited region disposed inwardly of corners of the pad to permit those portions of the backing film superimposed with marginal portions of the pad to be stretched or extended independently of those marginal portions, as described more fully hereinafter and disclosed in U.S. Letters Pat. No. 3,981,306. Furthermore, in dressings such as disposable diapers the shape of the backing film and the shape of the absorbent pad, the relationship between the backing film and the pad, and the attachment or adherence between the film and the pad all may be varied to provide different extensibility and conformability characteristics as will be described more fully hereinafter.

In still a different embodiment of the dressing of this invention the elastic and easily stretchable film material of the backing also is used for the facing which covers the opposite surface of the absorbent layer or pad. The elastic facing film is suitably shaped or perforated to define a multiplicity of holes or openings through which liquid may pass into the dressing to be absorbed by the pad. Since the facing film in this case is nonabsorbent, it also acts as a barrier which protects the wearer or user of a diaper, for instance, from direct contact with the wet pad. This form of the dressing of this invention is particularly conformable since both the backing film and the facing film are flexible, elastic and easily stretchable. Other porous or perforated extensible and elastic facing films also may be used in the dressing of this invention. As indicated hereinbefore, various types of extensible or stretchable nonwoven fabrics may be used as facings. In one preferred embodiment of a disposable diaper according to this invention the facing is an extensible nonwoven fabric which also is elastic. Fabrics of this general type are disclosed in U.S. Letters Pat. No. 3,485,706. A preferred form of this type of nonwoven fabric consists predominantly of entangled polyester fibrous elements. Various other dressing structures of this invention will be described more fully hereinafter.

As indicated hereinbefore, the film forming composition of this invention may comprise an elastomeric component and a resin component, and the elastomeric component may consist essentially of linear or radial A-B-A block copolymers or mixtures of these A-B-A block copolymers with simple A-B block copolymers. However, the proportion of A-B block copolymers in the mixture of A-B-A and A-B block copolymers should not exceed about 75 percent by weight and lower percentages normally would be used.

The A-B-A block copolymers of this invention are of the type which consist of A-blocks (end blocks) derived, i.e., polymerized or copolymerized, from styrene or styrene homologues; and B-blocks (center blocks) derived from conjugated dienes, such as isoprene or butadiene, or from lower alkenes, such as ethylene and butylene. Small proportions of other monomers also may enter into the block copolymers themselves. The individual A-blocks have a number average molecular weight of at least about 6,000, preferably in the range of about 8,000–30,000, and the A-blocks constitute about 5–50 percent, preferably about 10–30 percent, by weight of the block copolymer. The number average molecular weight of the B-blocks for linear A-B-A block copolymers preferably is in the range of about 45,000–180,000 and that of the linear copolymer, itself, preferably is in the range of about 75,000–200,000. The number average molecular weight of the radial A-B-A copolymers preferably is in the range of about 125,000–400,000. The designation A-B-A includes what are sometimes called A-B-C block copolymers wherein the end blocks are different from one another but both are derived from styrene or styrene homologues. This applies both to linear and radial block copolymers. The term "linear block copolymer" (or copolymers) includes branched A-B-A copolymers as well as unbranched A-B-A copolymers.

The radial A-B-A polymers useful in this invention are of the type described in U.S. Letters Pat. No. 3,281,383 and conform to the following general formula: $(A-B)_nX$, wherein A is a thermoplastic block polymerized from styrene or styrene homologues, B is an elastomeric block derived from conjugated dienes or lower alkenes, as indicated above, X is an organic or inorganic connecting molecule with a functionality of 2–4 as described in U.S. Pat. No. 3,281,383 or possibly with a higher functionality as described in the article entitled "New Rubber is Backed by Stars" appearing on page 35 of the June 11, 1975 issue of Chemical Week. "n" then is a number corresponding to the functionality of X.

The A-B block copolymers of this invention are of the type described in U.S. Letters Pat. Nos. 3,519,585 and 3,787,531 and comprise A and B-blocks derived from the monomers described hereinbefore in connection with the A-B-A copolymers.

The elastomeric component of the film forming composition of this invention may include small amounts of other more conventional elastomers but these should not exceed about 25 percent by weight of the elastomeric component. These other elastomers may include, highly broken down natural rubbers and butadiene-styrene random copolymer rubbers, synthetic polyisoprene, chloroprene rubbers, nitrile rubbers, butyl rubbers, and the like. Potentially elastomeric liquid polymers also may be employed as additives but normally in lower proportions not above about 10 percent by weight of the elastomeric component.

The resin component of this invention, if employed, consists essentially of low molecular weight resins which are adapted to associate principally with, and are principally compatible with, the thermoplastic A-blocks of the said block copolymers. These include low molecular weight resins based on poly-alpha-methylstyrene, polystyrene, polyvinyl toluene and similar aromatic resins, as well as copolymers thereof, coumarone indene and related cyclic compounds. Preferred resins for this purpose possess a number average molecular weight not above about 3,000 although higher molecular weight resins in the low weight range also may be employed. Small proportions, i.e., not above about 25 percent of the elastomeric component, of various other resins, which (if tack is desired) may include conventional tackifying resins such as hydrocarbon resins, rosin, hydrogenated rosin, rosin esters, polyterpene resins, and the like, also may be employed in the resin component of the film forming composition of this invention.

The film forming composition also may contain relatively small proportions of various other materials such as antioxidants, heat stabilizers and ultraviolet absorbers, release agents, extenders, fillers and the like. Typical antioxidants are 2,5 ditertiary amyl hydroquinone and ditertiary butyl cresol. Similarly, conventional heat stabilizers such as the zinc salts of alkyl dithiocarbamates may be used. Lecithin is one release material which has been found to be particularly suitable in minor amounts in this type of extrudable particulate mixture. However, waxes and various other release agents or slip agents also may be added in this manner. Relatively small proportions, in the neighborhood of 25 parts by weight of the elastomeric component, of various extenders such as higher molecular weight polystyrenes, nonreactive phenol-formaldehyde resins, linear polyester resins, polyethylene, polypropylene, etc., also may be included in the film forming composition of this invention. Similarly, the particulate mixture of this invention may include relatively small proportions, say 25 parts by weight of the elastomeric component, of fillers and pigments such as zinc oxide, aluminum hydrate, clay calcium carbonate, titanium dioxide, carbon black and others. Many of these fillers and pigments also may be used in powdered form as parting agents to be mixed with thermoplastic elastomer particles to prevent these particles from agglomerating prior to blending with resin particles and other materials.

Other and further features and advantages of the invention will appear to one skilled in the art from the following description, examples and claims, taken together with the drawings wherein:

FIG. 1 is a view in perspective of one embodiment of an absorbent dressing according to this invention wherein the dressing is in the form of a disposable diaper.

FIG. 2 is an enlarged partial sectional view along the line 2—2 of FIG. 1 adjacent one edge of the diaper.

FIG. 3 is a similarly enlarged broken sectional view of a diaper according to a slightly different embodiment of this invention.

FIG. 4 is another enlarged partial sectional view of a diaper according to still a different embodiment of the invention.

FIG. 5 is a cross sectional view through a portion of a molded corrugated absorbent layer which could be used in any of the foregoing embodiments of the invention.

FIG. 6 is a view in perspective of an adhesive bandage strip of a further embodiment of this invention.

FIG. 7 is a somewhat enlarged sectional view taken along the line 7—7 of FIG. 6.

FIG. 8 is a view in perspective of a sanitary napkin of another embodiment of this invention.

FIG. 9 is an enlarged sectional view taken along the line 9—9 of FIG. 8.

FIG. 10 is a top plan view of a disposable diaper according to another embodiment of this invention.

FIG. 11 is an enlarged broken sectional view taken along the line 11—11 of FIG. 10.

FIG. 12 is a somewhat reduced top plan view of still another embodiment of the diaper of this invention.

FIG. 13 is a top plan view of a disposable diaper according to a different embodiment of this invention.

FIG. 14 is a somewhat enlarged sectional view taken along the line 14—14 of FIG. 13.

FIG. 15 is a top plan view of another embodiment of a diaper according to this invention.

FIG. 16 is a somewhat enlarged sectional view taken along the line 16—16 of FIG. 15.

FIG. 17 is a top plan view of still another embodiment of the disposable diaper of this invention.

FIG. 18 is a similarly enlarged sectional view taken along the line 18—18 of FIG. 17.

Referring to the drawings, FIGS. 1 and 2 illustrate an absorbent disposable diaper 11, according to one embodiment of this invention, which comprises an extensible absorbent layer 12 laminated with an elastic and easily stretchable backing film 13 of this invention. The absorbent layer is covered by an extensible nonwoven fabric facing sheet 14 which extends across the opposite surface of the absorbent layer 12 to that which is in direct contact with the backing film 13. The backing film is folded around the longitudinal and transverse edges of the absorbent layer in the shape of a U in such a way that the top leg 15 of the U overlaps the extensible facing sheet 14. The backing film is heat sealed to the underside of the absorbent layer 12 by virtue of its high thermoplasticity, as well as to the top surface of the absorbent layer (through the facing sheet 14) in the segments designated by the letter S.

A somewhat different embodiment of a disposable diaper according to this invention is illustrated in FIG. 3 which shows a structure similar to that of FIGS. 1 and 2, except that the absorbent layer 12 terminates short of the longitudinal edges 16 of the backing film thereby providing flaps F at each side of the diaper. The extensible facing sheet 14 extends beyond the longitudinal edges of the absorbent layer and down into contact with the backing film where it is heat sealed thereto as indicated at S.

FIG. 4 illustrates another embodiment of the invention wherein the absorbent layer 12 terminates short of the longitudinal edges 16 of the backing film 13 to provide flaps F. In this construction the extensible facing sheet 14 extends around the edges of the absorbent layer 12 and thence between the absorbent layer 12 and the backing film 13 where it is heat sealed to both of them at S by virtue of the thermoplasticity of the film.

FIG. 5 illustrates one form of an extensible absorbent layer wherein an absorbent fibrous material is molded in the form of a compacted corrugated extensible sheet 18. Various other types of extensible or stretchable absorbent layer structures will suggest themselves to one skilled in the art. For instance, the absorbent layer may consist of several layers of highly creped paper or several layers of an extensible or crinkled nonwoven fabric or even a crinkled or chemically treated open woven gauze designed for high extensibility, and of course various layers of this type may be laminated with one another to form a composite extensible absorbent layer. Similarly, various types of extensible or stretchable nonwoven fabrics, webs or sheets may be used as a facing sheet to produce a stretchable and elastic disposable absorbent diaper or dressing according to this invention.

The pad or dressing is rendered extensible or stretchable, as explained above, by virtue of the properties of all of its members and the backing film is an important element of this. It is the novel elasticity of the backing film, however, taken together with its easy stretchability (low modulus), which make the diapers and dressings of this invention easily stretchable and highly conformable. Furthermore, when flaps F are provided at the edges of the dressing as illustrated in FIGS. 3 and 4, the flaps independently provide a high level of conformability which need not be present throughout the central portion of the dressing to the same extent.

Another illustration of the last cited structure is shown in FIGS. 6 and 7. Here an absorbent adhesive bandage 21 is depicted wherein an absorbent pad 22 is laminated with a strip of backing film 23 of this invention. The pad is placed in the center of the film strip and the strip presents adhesive surfaces 24 facing the pad on the flap portions of the film which extend between the pad 22 and the ends of the strip. As indicated above, these flaps are designated F. Similarly, the pad 22 is secured to the film by heat seals at S utilizing the high thermoplasticity of the film. As indicated hereinbefore and in the following examples, the backing films of this invention are not only elastic but highly extensible and easily stretchable as evidenced by the data given in the examples for elastic recovery, elongation to break and rubber modulus. An important advantage of the absorbent dressing of this invention, in the form shown in FIGS. 6 and 7 wherein adhesive flaps F of the backing film extend in opposite directions from the absorbent pad, is that the pad and the dressing may be released easily from the skin merely by pulling one end of the adhesive surfaced backing film longitudinally. In fact, in the thickness in which the backing film is used in adhesive bandages of the type shown, when one end of the adhesive film flap is pulled in this manner the bandage releases easily from the skin without hurting the user. This "ouchless" removal appears to be a function of the high extensibility (elongation to break) and easy stretchability (low rubber modulus) of the film-adhesive laminate, as explained more fully in my copending application Ser. No. 699,101, now U.S. Pat. No. 4,024,312. In this connection, the flaps of the backing film may be coated with an adhesive layer which provides the adhesive surfaces referred to, or the backing film itself may be so designed as to be adhesive on one side and nonadhesive on the other.

FIGS. 8 and 9 illustrate a sanitary napkin 30 according to this invention wherein an absorbent layer or core 31 is surrounded by a nonwoven fabric facing material which is covered on one side with a thermoplastic elastic film 32 of this invention. As shown in FIGS. 8 and 9 the napkin is inverted from the use position to show the location of the film in FIG. 8. It will be seen that the nonwoven fabric is in two pieces, i.e., a wrapper 33 which extends around the pad and a cover 34 which fits underneath the film 32 in overlapping relationship with the ends of the wrapper. The backing film, in turn, overlaps the cover 34 so that it also contacts the wrapper 33 directly. The wrapper, the cover and the backing film are held together by heat seals S formed by using the thermoplasticity of the backing film.

In the sanitary napkin of FIGS. 8 and 9 the backing film 32 acts as a barrier which blocks the passage of liquids and as a friction surface which holds the napkin in position in clothing provided for this purpose. It is a feature of the backing film of this invention that it may be designed to have a relatively high coefficient of friction, i.e., a dynamic friction coefficient of above about one, although higher coefficients of friction may easily be developed as indicated hereinafter in the examples.

FIGS. 10 and 11 illustrate a disposable diaper 35 according to another embodiment of the invention which comprises a rectangular absorbent layer or pad 12, an elastic and easily stretchable backing film 13 of this invention and a porous or perforated extensible and elastic facing film 36. The porous facing film 36 may be a perforated sheet of the same material as the highly elastic backing film 13 or it may be a porous reticular web of the type described in my copending application Ser. No. 699,102 filed June 23, 1976, now U.S. Pat. No. 4,062,995, i.e., a permanently heat shaped elastic and thermoplastic reticular web comprising strands intersecting in a pattern and defining a corresponding pattern of holes.

The backing film 13 and the facing film 36 are shaped in such a way that they extend beyond the edges of the absorbent pad 12 where they overlap to form transversely extending flaps 37 at each corner of the diaper as indicated by the letter F in FIG. 11. The backing film 13 and the porous facing film 36 are sealed to one another where they overlap beyond the pad as indicated by the letter S. This includes the flap areas 37. As indicated hereinbefore, one of the advantages of the preferred form of elastic backing film of this invention is that it is highly thermoplastic and easily heat sealable and when the same material is used in the backing and facing films, 13 and 36, these films may be heat sealed together very easily at low temperatures and therefore remain highly flexible where sealed together in the flaps 37.

As shown most clearly in the enlarged portions of FIGS. 10 and 11, the facing film 36 presents a muliplicity of spaced small pores or openings 38. The size and spacing of these openings 38 is such that liquids may pass easily through the openings into the pad 12 where they are absorbed. The facing film 36 between the openings 38 is nonabsorbent and therefore becomes generally dry after the liquid enters the pad 12. This is one advantage of this embodiment of the diaper of this invention as compared with diapers utilizing an absorbent facing.

Another advantage of this diaper is that the flaps 37, like the flaps F of FIGS. 3 and 6, are fully elastic and extensible independently of the absorbent pad 12. Furthermore these flaps 37 are highly elastic and easily extensible because they consist of the highly elastic and extensible film of this invention both in the backing and in the facing. Thus, the absorbent pad 12 may be sealed to the backing film 13 and/or the facing film 36 at the four corners of the pad 12 without preventing the flaps 37 from being extensible independently of the pad 12 in the direction of the interface between the backing film 13 and the pad 12.

FIG. 12 illustrates still another embodiment of the diaper of this invention. This diaper 40 is similar to that of FIGS. 10 and 11 but with the overlapping facing layer 41 and backing film, not shown, being shaped to provide flaps 42 beyond opposite edges of the absorbent pad 12 at only one end of the diaper. The facing layer 41 is an extensible non-woven fabric consisting predominantly of entangled polyester fibrous elements of the type described in U.S. Letters Pat. No. 3,485,706. The fabric is heat sealed to the elastic backing film in flaps 42 with the result that the flaps are highly elastic and easily stretchable independently of the absorbent layer 12 which may be adhered to or heat sealed to the backing layer substantially across its surface in any desired manner.

FIGS. 13 and 18 illustrate different embodiments of diapers according to this invention wherein the absorbent pad 12 is attached to the backing film 13 over only a limited region disposed inwardly of corners of the pad to permit those portions of the backing film 13 superimposed with marginal portions of the pad, i.e., portions adjacent the corners of the pad, to be stretched independently of those portions of the pad.

For instance, in the embodiment of FIGS. 13 and 14 the absorbent pad 12 is attached to the backing film only through a heat seal between the film and the pad in the relatively small area 44 located in the center of the diaper and indicated in FIG. 14 by the Letter S. The facing layer in this case is a porous, elastic and thermoplastic film of the type described in connection with FIGS. 10 and 11 and which is heat sealed to the marginal portions of the backing film 13 beyond the edges of the pad 12 but otherwise unattached to the backing. The backing film 13 and the facing film 36 also are sealed to one another at the extensions in the upper corners of the diaper, as shown in FIG. 13, to form flaps 45 to facilitate securing the diaper in use. However, the backing and facing films 13 and 36 are stretchable in the plane of the interface between the pad and the backing in the entire area falling outside the central sealing area 44, including the areas of the flaps 45 but not limited thereto.

FIGS. 15 and 16 illustrate a straight line seal 46 between the absorbent pad 12 and the backing film 13 which extends along the vertical centerline of the diaper. As a result, the backing and facing films 13 and 36 are free to be stretched laterally independently of the pad 12 in the entire areas on each side of the seal line 46, or seal S in FIG. 16, including of course the areas of flaps 47 wherein the backing and facing films are sealed together at the lower corners of the diaper as shown in FIG. 15.

FIGS. 17 and 18 illustrate a diamond shaped seal 49 between the backing film 13 and the absorbent layer 12, with the result that all four corners of the pad 12 are unattached to the backing film 13 or to the facing film 36 so that the corresponding portions of these films are free to be stretched laterally or longitudinally of the diaper independently of the pad 12. Additionally, those overlapping portions of the backing and facing films which are sealed to one another as indicated at S in the flap areas F on either side of the diaper also are free to be stretched laterally or longitudinally independently of the pad.

The following examples of the backing films useful in absorbent dressings according to this invention are given only by way of illustration and are not intended to limit the scope of the invention in any way. Table A gives the film compositions for Examples I-III together with the physical characteristics of the films. In the examples, all proportions are expressed in parts per one hundred parts by weight of the total elastomeric component unless otherwise indicated.

Film thickness is expressed in mils, or thousandths of an inch, tensile strength is pounds per square inch to break the film as measured on an Instron tensile tester with an initial jaw separation of one inch at a speed of twelve inches per minute, and elongation is the percentage which the film must be stretched in a given direction to break it, i.e., stretched dimension at break minus normal dimension, over normal dimension in that direction, times a hundred. In all cases the designation "M.D." means "machine direction" lengthwise in the direction of processing and "C.D." means "cross direction."

Elastic recovery is precentage of immediate recovery in length after being stretched fifty (50) percent of original length and then released to allow free return. It is a function of the amount of stretch recovered over the amount of stretch. The amount of stretch equals the length when stretched minus the original length and the amount of stretch recovered equals the length when stretched minus the length after recovery. Rubber modulus is tensile stress in pounds per square inch of initial cross section measured at one half inch extension per inch of length or 50 percent elongation. This also is called 50 percent rubber modulus.

Gurley stiffness is measured as an opposite or inverse measure of flexibility with a standard Gurley stiffness tester using 1.0 by 1.5 inch samples with ¼ inch of sample in the jaw and ¼ inch overlapping the blade. The measured Gurley stiffness then is converted to stiffness at a thickness of one mil by dividing the measured stiffness by the cube of the measured thickness in mils. The coefficient of sliding friction is measured by drawing the film samples horizontally over a chrome plated smooth metal panel with a 500 gram weight on top of the film. This is done in a TLMI adhesion tester at a pulling speed of 12 inches per minute.

Heat sealability is measured by clamping each film sample in an open sandwich with a sheet of standard fiberboard test material between the jaws of an Erich International Corporation Bag Sealer at 42 p.s.i. air pressure. The fiberboard is Standard Reference Material 1810 specified in United States Department of Commerce Standard for Tape Adhesion Testing No. 16 (M:L-B-131E, Class 2). One of the jaws is heated and the other is unheated. The boxboard is placed in contact with the heated jaw and the film in contact with the unheated jaw. Both jaws are cooled to ambient temperature by air jets prior to clamping. When the test material is in position between the jaws, the bottom jaw is heated by an electric heater to seal the film to the boxboard by heat transferred through the board. The heating time period required to heat the lower jaw to the minimum peak temperature necessary to permanently heat seal the film of the boxboard, using a clamping period of 4 seconds, then is measured. The minimum peak permanent heat sealing temperature corresponding to the time recorded, then is obtained by reference to a time-temperature calibration curve for the instrument obtained by measuring temperatures at the bonding surface of the boxboard. The minimum peak temperature referred to is that reached at the time the electric heater is deenergized at the end of the heating time period.

TABLE A

| Ingredients & Characteristics | Examples | | |
|---|---|---|---|
| | I | II | III |
| Kraton 1107 S-I-S Linear Copolymer | 100 | | 100 |
| Solprene 420 S-I-S Radial Copolymer | | 100 | |
| Amoco 18-210 Resin | | | 150 |
| Amoco 18-290 Resin | 100 | 100 | |
| Zinc Dibutyl Dithiocarbamate (Antioxidant) | 1 | 2 | 1 |
| 2,5 Ditertiary Amyl Hydroquinone (Antioxidant) | ½ | ½ | ½ |
| Titanium Dioxide Pigment | 5 | | |
| Thickness, (Mils) | 3.6 | 4.2 | 3.0 |
| Rubber modulus at 50% Elongation, lbs./in.$^2$ | 800 | 115 | 475 |
| Elongation (M.D.), % | 530 | 1200 | 2100 |
| Elongation (C.D.), % | 750 | 1140 | 1260 |
| Tensile Strength (M.D.), lbs./in.$^2$ | 1220 | 600 | 900 |
| Tensile Strength (C.D.), lbs./in.$^2$ | 1050 | 570 | 970 |
| Gurley Stiffness, mg./in.$^2$/mil | 0.38 | 0.42 | 0.05 |
| Heat Sealing Temperature, °F. | 250 | 240 | 250 |
| Friction Coefficient (Dynamic) | 2.58 | 2.60 | 2.23 |
| % Elastic Recovery After 50% Elongation | 98 | 95 | 95 |

It will be seen that the films of all of the above examples are highly elastic, i.e., possess an elastic recovery after 50 percent elongation of well above about 90 percent. Furthermore, all the films possess a low rubber modulus, in these examples, not above about 1,000 lbs./in.$^2$ at 50 percent elongation.

The films of the examples are not particularly oriented as evidenced from the tensile strength readings in the machine and cross-directions and generally possess a high elongation, i.e., at least about 500 percent in both directions.

The films are highly flexible, exhibiting Gurley stiffness readings as low as 0.05 mg./in.$^2$/mil and no higher than 0.42 mg./in.$^2$/mil. They also are not slippery, i.e., they possess a dynamic coefficent of friction well above 0.5, more specifically between 2 and 3. The maximum permanent heat sealing temperature determined as described hereinbefore is about 250° F., well below 350° F.

In the foregoing examples Kraton 1107 copolymer is a thermoplastic elastomeric A-B-A (styrene-isoprene-styrene) block copolymer of this invention offered by the Shell Chemical Company, wherein the styrene content (that of the A-blocks) is about 12-15 percent, closer to 15 percent by weight of the block copolymer, and the polymer possesses a solution viscosity of about 2,000 centipoises at 25 percent solids in toluene at room temperature (using a Brookfield Viscometer with a No. 4 spindle at 60 r.p.m.), and a number average molecular weight of about 110,000–125,000. Solprene 420 copolymer is a radial styrene-isoprene-styrene block copolymer of the type described hereinbefore which has a number average molecular weight of 240,000 and a styrene content of about 15 percent.

Amoco 18-210 and 18-290 resins are solid polyalphamethylstyrenes offered by Amoco Chemical Co., with softening points of about 210° F. (99° C.) and 290° F. (143° C.) respectively.

Having now described the invention is specific detail and exemplified the manner in which it may be carried into practice, it will be readily apparent to those skilled in the art that innumerable variations, applications, modifications, and extensions of the basic principles involved may be made without departing from its spirit or scope.

What is claimed is:

1. A highly flexible and conformable disposable absorbent dressing which comprises a layer of absorbent material, and a thin, flexible, elastic and easily stretchable thermoplastic backing film retained in superimposed relationship with said absorbent layer, said backing film possessing:
   1. an elastic recovery from 50 percent stretch of at least about 75 percent, 2. a rubber modulus of not above about 2,000 pounds per square inch at 50 percent elongation, and 3. a Gurley stiffness at a thickness of 1 mil of not above about one.

2. An absorbent dressing according to claim 1, wherein the backing film possesses permanent heat-sealability to fiberboard when pressed together with said fiberboard for a period no longer than 4 seconds at a peak temperature of not above about 350° F. at the interface between the film and the fiberboard as described herein.

3. An absorbent dressing according to claim 2, wherein the absorbent layer and the backing film are retained in superimposed relationship with one another by heat seals formed by said film.

4. An absorbent dressing according to claim 1, wherein the absorbent layer and the backing film are substantially coextensive in the direction of the plane of their interface.

5. An absorbent dressing according to claim 1, wherein portions of the backing film are extensible independently of the absorbent layer in the direction of the plane of the interface between the backing film and the absorbent layer.

6. An absorbent dressing according to claim 5, wherein the backing film overlaps the absorbent layer a substantial amount in the direction of the plane of their interface to form opposed flaps of the film at opposite sides of the absorbent layer, said flaps being elastic, easily stretchable and highly extensible.

7. An absorbent dressing according to claim 6, wherein the backing film possess a lengthwise elongation to break of at least about 300 percent and said flaps are adapted to adhere to the skin or other application surface or to one another and to be detached easily therefrom by stretching the flaps.

8. An absorbent dressing according to claim 6, wherein the flaps present pressure-sensitive adhesive major surfaces on the surface of the film facing the absorbent layer.

9. An absorbent dressing according to claim 6, wherein both surfaces of the film are normally nontacky but are adapted to adhere firmly to any portion of the film itself when pressed into contact therewith.

10. An absorbent dressing according to claim 1, wherein said film is formed from an elastomeric and thermoplastic film forming composition which comprises an elastomeric component and 0-200 parts of a resin component per one hundred parts by weight of the elastomeric component; said elastomeric component consisting essentially of linear or radial A-B-A block copolymers or mixtures of these linear or radial A-B-A copolymers with simple A-B block copolymers, said A-blocks being derived from styrene or styrene homologues and said B-blocks being derived from conjugated dienes or lower alkenes; said resin component consisting essentially of lower molecular weight resins adapted to associate principally with the thermoplastic A-blocks of said block copolymers.

11. An absorbent dressing according to claim 10, wherein the film forming composition comprises about 85 to about 200 parts of the resin component per one hundred parts by weight of the elastomeric component.

12. An absorbent dressing according to claim 10, wherein the B-blocks are derived from isoprene.

13. An absorbent dressing according to claim 1, which further comprises a porous and extensible facing layer covering the opposite surface of the absorbent layer to that covered by said backing film.

14. An absorbent dressing according to claim 13, wherein said facing layer is elastic and easily stretchable 15. An absorbent dressing according to claim 14, wherein said facing layer is a porous film possessing elasticity and extensibility properties equivalent to those of the backing film.

16. An absorbent dressing according to claim 14, wherein said facing layer is formed from the same material as the backing film.

17. An absorbent dressing according to claim 14, wherein said facing layer is formed from an elastomeric and thermoplastic film forming composition which comprises an elastomeric component and 0-200 parts of a resin component per one hundred parts by weight of the elastomeric component; said elastomeric component consisting essentially of linear or radial A-B-A block copolymers or mixtures of these linear or radial A-B-A copolymers with simple A-B block copolymers, said A-blocks being derived from styrene or styrene homologues and said B-blocks being derived from conjugated dienes or lower alkenes; said resin component consisting essentially of low molecular weight resins adapted to associate principally with the thermoplastic A-blocks of said block copolymers.

18. An absorbent dressing according to claim 17, wherein said facing layer is a permanently heat shaped elastic and thermoplastic reticular web comprising strands intersecting in a pattern and defining a corresponding pattern of holes.

19. An absorbent dressing according to claim 14, wherein said facing layer is a nonwoven fabric.

20. An absorbent dressing according to claim 19, wherein said nonwoven fabric consists predominantly of entangled polyester fibrous elements.

21. An absorbent dressing according to claim 14, wherein the facing layer and the backing film extend beyond the edges of the absorbent pad in the direction of the plane of the interface between the film and the pad to form flaps at opposite edges of said pad which are extensible independently of the pad.

22. An absorbent dressing according to claim 21, wherein said backing film and said facing layer are heat sealed in overlapping relation to one another to form said flaps.

23. An absorbent dressing according to claim 1, wherein the backing film possesses an elastic recovery from 50 percent stretch of at least about 90 percent.

* * * * *